US012642457B2

(12) United States Patent
Gutierrez-Osuna et al.

(10) Patent No.: US 12,642,457 B2
(45) Date of Patent: Jun. 2, 2026

(54) PREDICTING FOOD MACRONUTRIENTS FROM BLOOD BIOMARKERS

(71) Applicant: The Texas A&M University System, College Station, TX (US)

(72) Inventors: Ricardo Gutierrez-Osuna, College Station, TX (US); Jack Bobak Mortazavi, Bryan, TX (US); Zepeng Huo, College Station, TX (US); Gerard L. Coté, College Station, TX (US); Nicolaas E. Deutz, College Station, TX (US)

(73) Assignee: The Texas A&M University System, College Station, TX (US)

( * ) Notice: Subject to any disclaimer, the term of this patent is extended or adjusted under 35 U.S.C. 154(b) by 847 days.

(21) Appl. No.: 16/871,030

(22) Filed: May 10, 2020

(65) Prior Publication Data

US 2020/0352481 A1 Nov. 12, 2020

Related U.S. Application Data

(60) Provisional application No. 62/846,520, filed on May 10, 2019.

(51) Int. Cl.
| | |
|---|---|
| *A61B 5/145* | (2006.01) |
| *G01N 33/02* | (2006.01) |
| *G16B 5/00* | (2019.01) |
| *G16B 50/30* | (2019.01) |

(52) U.S. Cl.
CPC ......... *A61B 5/14532* (2013.01); *G01N 33/02* (2013.01); *G16B 5/00* (2019.02); *G16B 50/30* (2019.02)

(58) Field of Classification Search
None
See application file for complete search history.

(56) References Cited

U.S. PATENT DOCUMENTS 6,379,301 B1 * 4/2002 Worthington ........ A61B 5/7275
128/920

OTHER PUBLICATIONS

Dassau, Eyal, et al. "Detection of a meal using continuous glucose monitoring: implications for an artificial β-cell." Diabetes care 31.2 (2008): 295-300.*
Rowe, John W., et al. "Characterization of the insulin resistance of aging." The Journal of clinical investigation 71.6 (1983): 1581-1587.*
Esko, Toñu, et al. "Metabolomic profiles as reliable biomarkers of dietary composition1-3." The American journal of clinical nutrition 105.3 (2017): 547-554.*

* cited by examiner

Primary Examiner — G. Steven Vanni
(74) Attorney, Agent, or Firm — Jackson Walker LLP

(57) ABSTRACT
A method of predicting a composition of a meal includes obtaining data relating to concentration of a biomarker of an individual that consumed the meal, analyzing the data to determine the composition of the meal, wherein the analyzing comprises using a computational model. The computational model relies upon statistical learning techniques to breakdown meal composition into macronutrient levels.

10 Claims, 5 Drawing Sheets

(b) Varying Proteins (a) Varying Carbohydrates (d) All Responses to C2P2F2

(c) Varying Fats

PREDICTING FOOD MACRONUTRIENTS FROM BLOOD BIOMARKERS

CROSS-REFERENCES TO RELATED APPLICATIONS

This application claims the benefit of priority to and incorporates by reference the entire disclosure of U.S. Provisional Patent Application No. 62/846,520 filed on May 10, 2019.

STATEMENT REGARDING FEDERALLY SPONSORED RESEARCH

This invention was made with government support with funding from the National Science Foundation Engineering Research Center for Precise Advanced Technologies and Health Systems for Underserved Populations (PATHS-UP) (Award #1648451). The government has certain rights in the invention.

BACKGROUND

Thirty million Americans live with diabetes, and another 80 million have pre-diabetes, a condition that left untreated often leads to diabetes. Diabetes occurs when blood sugar is too high due to poor nutrition (e.g., too many refined carbohydrates) and/or inadequate insulin regulation (i.e., insulin resistance). Sustained high levels of blood glucose can have disastrous long-term health consequences, including cardiovascular diseases (the main cause of death in the developed world), retinopathy (leading to blindness), peripheral neuropathy (leading to limb amputations), and nephropathy (kidney damage). An essential component of clinical interventions for diabetes is monitoring dietary intake. However, conventional methods for diet tracking rely on human recall and/or manual input, which are inaccurate and burdensome—regardless of the medium used for logging (i.e., paper or electronic). Various sensing techniques have been explored to capture dietary intake, such as wearable sensors (microphones, accelerometers) to detect eating behaviors such as hand-to-mouth gestures and chewing/swallowing, or computer vision techniques to recognize food items and ingredients from photographs. These methods reduce the burden to the user, but are inaccurate and unreliable.

A unique and unexplored opportunity to solve this problem has emerged with the advent of wearable and implantable sensors to measure various biomarkers and physiological signals in the body. A good example is the use of continuous glucose monitors (CGMs) to measure fluctuations in blood glucose throughout the day and after a meal. A CGM includes a small electrode inserted under the skin (subcutaneously) and a transmitter that sends the information to a monitoring device. CGMs have gained acceptance to manage type-1 diabetes but have yet to make an impact in type-2 diabetes mellitus (T2DM), by far the more predominant of the two diseases (90%), or as an enabling technology to measure dietary intake in individuals at risk of developing diabetes. What makes CGMs particularly appealing for the proposed work is the fact that the glucose response to a meal depends on its macronutrient composition (carbohydrates, proteins, fats, fiber); as an example, combining protein and fat with carbohydrates generally leads to smaller increases and slower decreases of glucose concentrations. This suggests that the shape of the glucose response to a meal can be used to recover the macronutrient composition of the meal, and therefore be used to log food intake automatically.

SUMMARY

This summary is provided to introduce a selection of concepts that are further described below in the detailed description. This summary is not intended to identify key or essential features of the claimed subject matter, nor is it to be used as an aid in limiting the scope of the claimed subject matter.

An example of a method of predicting a composition of a meal includes obtaining data relating to concentration of a biomarker of an individual that consumed the meal, analyzing the data to determine the composition of the meal, and wherein the analyzing includes using a computational model.

In embodiments of the method of predicting a composition of a meal, the computational model predicts an amount of macronutrients of the meal.

In embodiments of the method of predicting a composition of a meal, the macronutrients comprise one or more of carbohydrates, proteins, fats, and fiber.

In embodiments of the method of predicting a composition of a meal, the biomarker comprises one or more of a sugar, an amino acid, a lipid, an electrolyte, a mineral, a vitamin, or a metabolite.

In embodiments of the method of predicting a composition of a meal, the biomarker is measured with wearable or implantable sensors.

In embodiments of the method of predicting a composition of a meal, a feature relating to a concentration of the biomarker over time is measured.

In embodiments of the method of predicting a composition of a meal, the feature comprises one of: area under-the-curve, an amount of time for the concentration of the biomarker to reach peak value after the meal is consumed, an amount of time for the concentration of the biomarker to return to a baseline value, a slope value describing a response of the biomarker after the meal is consumed, and a shape of the response of the biomarker.

In embodiments of the method of predicting a composition of a meal, the feature is normalized relative to a baseline level of the biomarker of the individual.

In embodiments of the method of predicting a composition of a meal, the computational model comprises statistical learning techniques.

In embodiments of the method of predicting a composition of a meal, the biomarker is glucose and is measured with a continuous glucose monitor.

In embodiments of the method of predicting a composition of a meal, the continuous glucose monitor logs the composition of the meal.

In embodiments of the method of predicting a composition of a meal, the computational model uses Gaussian kernels to capture a shape of a response of the biomarker and its area under the curve.

In embodiments of the method of predicting a composition of a meal, the analyzing includes normalizing a response of the biomarker relative to a physiological parameter of the individual, such as body composition or total weight.

In embodiments of the method of predicting a composition of a meal, responsive to the determination of the composition of the meal, the individual changes an amount of a macronutrient in a future meal.

In embodiments of the method of predicting a composition of a meal, responsive to the determination of the composition of the meal, an amount of a prescribed medicine is changed.

BRIEF DESCRIPTION OF THE DRAWINGS

A more complete understanding of the subject matter of the present disclosure may be obtained by reference to the following Detailed Description when taken in conjunction with the accompanying Drawings wherein:

FIGS. 4A-4D are graphs showing glucose level versus time with: FIG. 4A showing glucose response at increasing levels of carbohydrates, with protein and fat at fixed levels; FIG. 4B showing glucose response at increasing levels of protein, with carbohydrates and fat at fixed levels; FIG. 4C showing glucose response at increasing levels of fat, with carbohydrates and protein at fixed levels; and FIG. 4D showing individual variability for the C2P2F2 meal. X axis are samples (taken every 15 minutes) and Y axis are the blood glucose values.

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

Prediction of the macronutrients of a consumed meal can be accomplished by analyzing changes in the concentration of one or more biomarkers of an individual after consumption of the meal. Various biomarkers may be analyzed and data describing the biomarkers may logged or recorded (e.g., into a database or the like). In some embodiments, a single biomarker of an individual is analyzed and can include, for example, sugars (e.g., glucose), amino acids, lipids, electrolytes, minerals, vitamins, and metabolites. In some embodiments, multiple biomarkers may be analyzed, which can increase the accuracy of the macronutrient predictions.

Figure 1:
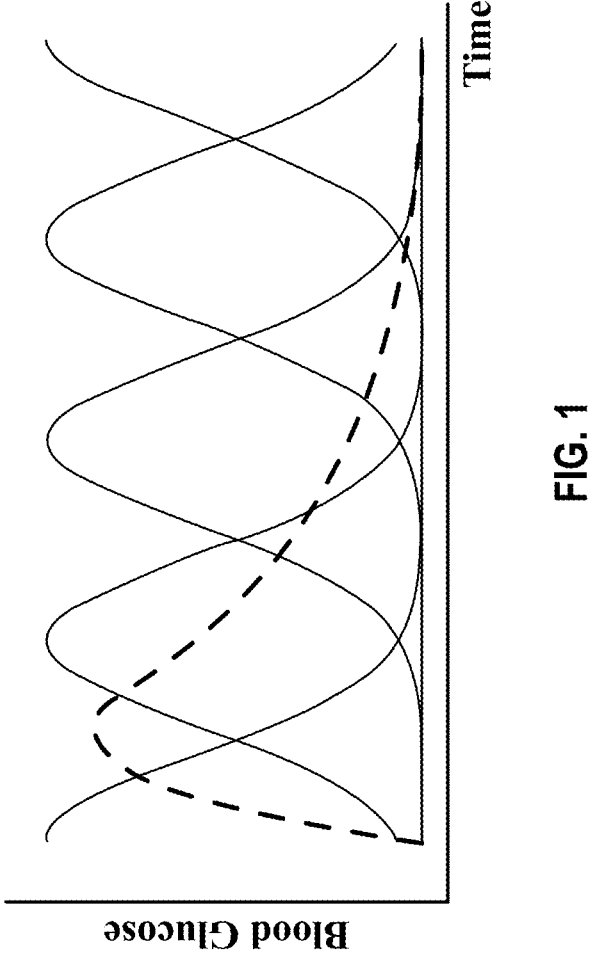
FIG. 1 is a graph showing the extraction of five Gaussian area under the curve features, with fasting glucose subtracted to generate relative area under the curve values, over an eight hour window.

By way of example, a plasma glucose response to a meal may be used as a biomarker. The plasma glucose response depends on the macronutrient composition (i.e., carbohydrates, proteins, fats, fibers) of the consumed meal. For example, combining fat and protein with carbohydrates generally leads to smaller increases and slower decreases of glucose concentrations. This suggests that the shape of the biomarker response to a meal can be used to recover the macronutrient composition of the meal, and can therefore be used to log food intake automatically (e.g., by the monitoring device of the CGM or by a separate logging device in communication with the CGM, such as a mobile application on a mobile device). The biomarker response may be captured or interpreted in various ways. Using glucose as a biomarker as an example, FIG. 1 illustrates a post-prandial response (i.e., response after a meal), from which one could extract a number of features such as an area under-the-curve (AUC), time to peak value (e.g., the time it takes the biomarker to increase from its baseline or pre-meal value to its peak post-prandial value), time to return to baseline (e.g., the time it takes the biomarker to decrease from its peak post-prandial value to its baseline or post-prandial value), slopes describing the response (e.g., slopes as determined from a graph of the biomarkers concentration over time), and shape of the post-prandial response of the biomarker. Based on these findings, a personalized meal prediction using, for example, CGM recordings, daily habits, and person profiling is possible.

WORKING EXAMPLES

Several computational models were developed and tested. The computational models may use, for example, a number of statistical learning techniques such as regression analysis, classification and clustering. In this application, we examine three embodiments based on multi-task neural networks or gradient boosted tree regression, but other computational models may be used as well. Each computational model is discussed in more detail below.

To build the computational models, we recruited fifteen healthy subjects (not diagnosed with T2DM or pre-diabetes) ages 60-85 years and Body Mass Index (BMI) in the range of 25-35 to participate in a clinical study. Each subject participated in nine study days in which they consumed a predefined meal in a randomized design. The composition of the nine meals is shown in Table 1. Each study day lasted approximately eight hours and the procedures on the study days were identical, with the only change being the macronutrient composition of the meal taken (e.g. varying values of carbohydrates, proteins, and fats). In what follows, we use the notation C?P?F?, where ? represents the amount of each macronutrient in the meal (1: low; 2: medium; 3: high). Subjects were asked to fast for at least eight hours prior to the meal intake on each study day, so that the first blood glucose reading would be their fasting glucose. A continuous glucose monitor was placed on the first study day and replaced every two weeks. After taking a baseline blood sample the morning of a study visit, a predefined meal was consumed. Subjects were then asked to remain in a sedentary state and were not allowed to eat anything for the following eight hours to remove impact of physical activity on the glucose response. Small arterialized venous blood samples (5 ml) were subsequently drawn at time 15, 30, 45, 60, 90, 120, 180, 240, 300, 360, 420, and 480 minutes (13 blood samples). Plasma concentration of amino acids, fatty acids, and insulin were measured from these blood samples using liquid chromatography-mass spectrometry.

Figure 4B:
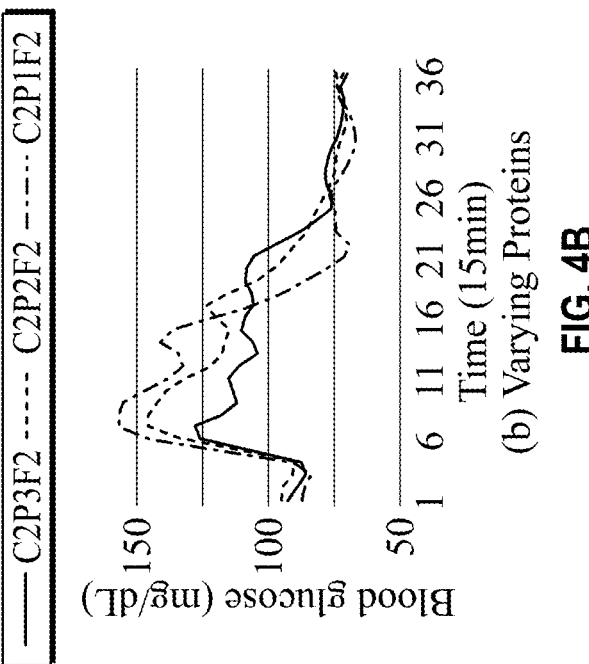
Figure 4A:
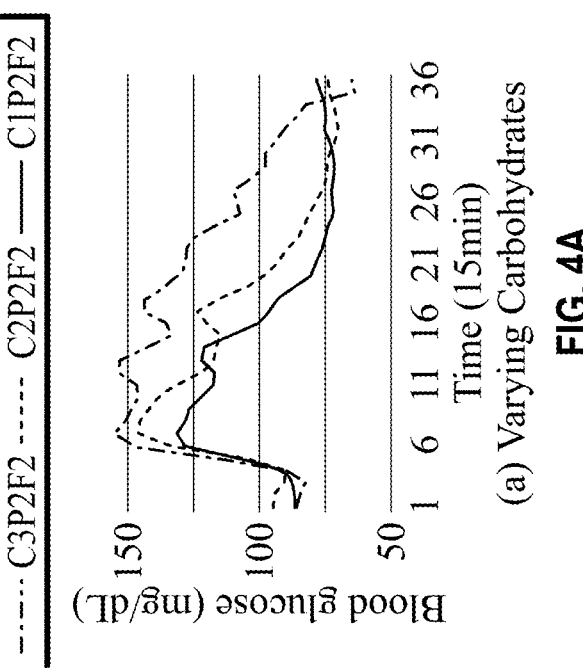
Figure 4D:
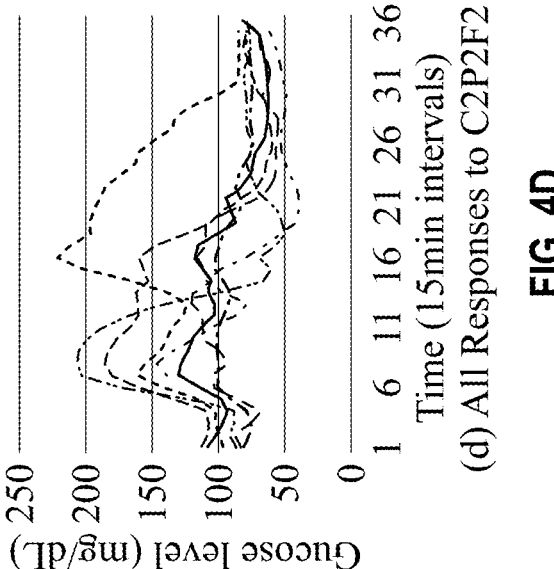
Figure 4C:
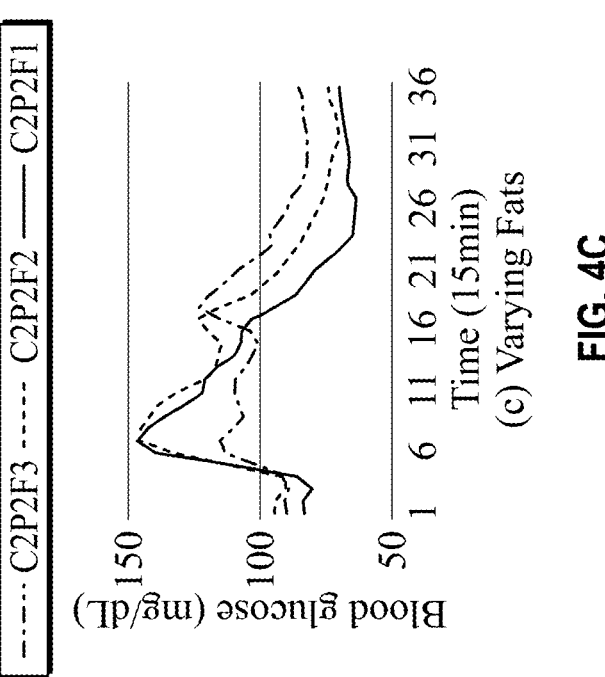

FIGS. 4A-4D illustrate the meal-to-meal variability due to modifying the meal macronutrients and the subject-to-subject variability that exists within the same meal. FIG. 4A shows the average response across subjects as the amount of carbohydrates (C1, C2, C3) increases while maintaining the other two macronutrients at a fixed level (P2, F2). As shown, the glucose response becomes more pronounced at higher levels of carbohydrates, both in terms of the maximum value and the overall AUC. FIG. 4B shows the average response across subjects as the amount of protein (P1, P2, P3) increases while maintaining the other two macronutrients at a fixed level (C2, F2). As the amount of protein increases, the glucose response becomes more moderate, with lower maximum levels and slower return to the baseline. FIG. 4C shows the average response across subjects as the amount of fat (F1, F2, F3) was increased while maintaining the other two macronutrients at a fixed level (C2, P2). As in the case for protein, when the amount of fat was increased, the glucose response became more moderate, with lower maximum levels and slower return to the baseline. These results show that the shape of the glucose response depends on the constituents of the meal. FIG. 4D shows the response of each participant to the C2P2F2 meal, which illustrates the high level of variability and the need to develop personalized models.

TABLE 1

Composition of Meals in the Study

| Meal | Carbohydrate (g) | Protein (g) | Fat (g) |
|---|---|---|---|
| C1P1F1 | 52.25 | 15 | 13 |
| C2P2F2 | 94.75 | 30 | 26 |
| C3P3F3 | 179.75 | 60 | 52 |
| C1P2F2 | 52.25 | 30 | 26 |
| C3P2F2 | 179.75 | 30 | 26 |
| C2P3F2 | 94.75 | 60 | 26 |
| C2P1F2 | 94.75 | 15 | 26 |
| C2P2F3 | 94.75 | 30 | 52 |
| C2P2F1 | 94.75 | 30 | 13 |

As shown in FIG. 4A, the overall shape of the postprandial glucose response (PPGR) follows a characteristic pattern with an initial rise about 10-15 minutes after the meal, a peak after about 90 minutes, and a slowed decline towards the baseline. The specifics depend largely on the composition of the meal and also on the metabolism of the individual. A number of features or parameters have been proposed to capture information about the shape of the response, such as the peak glucose values, peak time and rates of increase and decrease to and from the peak. In the present implementation, a feature extraction approach was selected to be robust to sensor noise and has been successfully used to extract information from gas sensor transients. The approach consists of placing a family of Gaussian kernels uniformly over the time axis in the PPGR and determining the AUCs. These AUC features captured the initial rise time of the PPGR, duration of the elevated glucose level, and the recovery back to the baseline glucose level. Formally, denoting the PPGR by g(t), each AUC feature x(i) is computed as:

$$x(i) = \int_0^T (g(t) - g(0))e^{-\frac{1}{2\sigma_k^2}(t-T_k)} dt \qquad \text{Equation 1}$$

where T is the duration of the PPGR (8 hours in our case), $T_k$ is the center position of the kernel in the time domain, $$\sigma_k^2$$

is its spread, and g(0) is the baseline glucose level, which we subtract since it is strongly tied to each individual's physiology. Different numbers of kernels can be used, to capture shape information with different degrees of resolution. In an initial exploration, we evaluated using families of 3, 5 and 9 Gaussian kernels (and their combinations), but empirically settled for a family of D=5 kernels, as illustrated in FIG. 1. To account for individual differences, these AUC features were normalized relative to their maximum and minimum levels on each subject.

1. Multi-Task Neural Network

Figure 2:
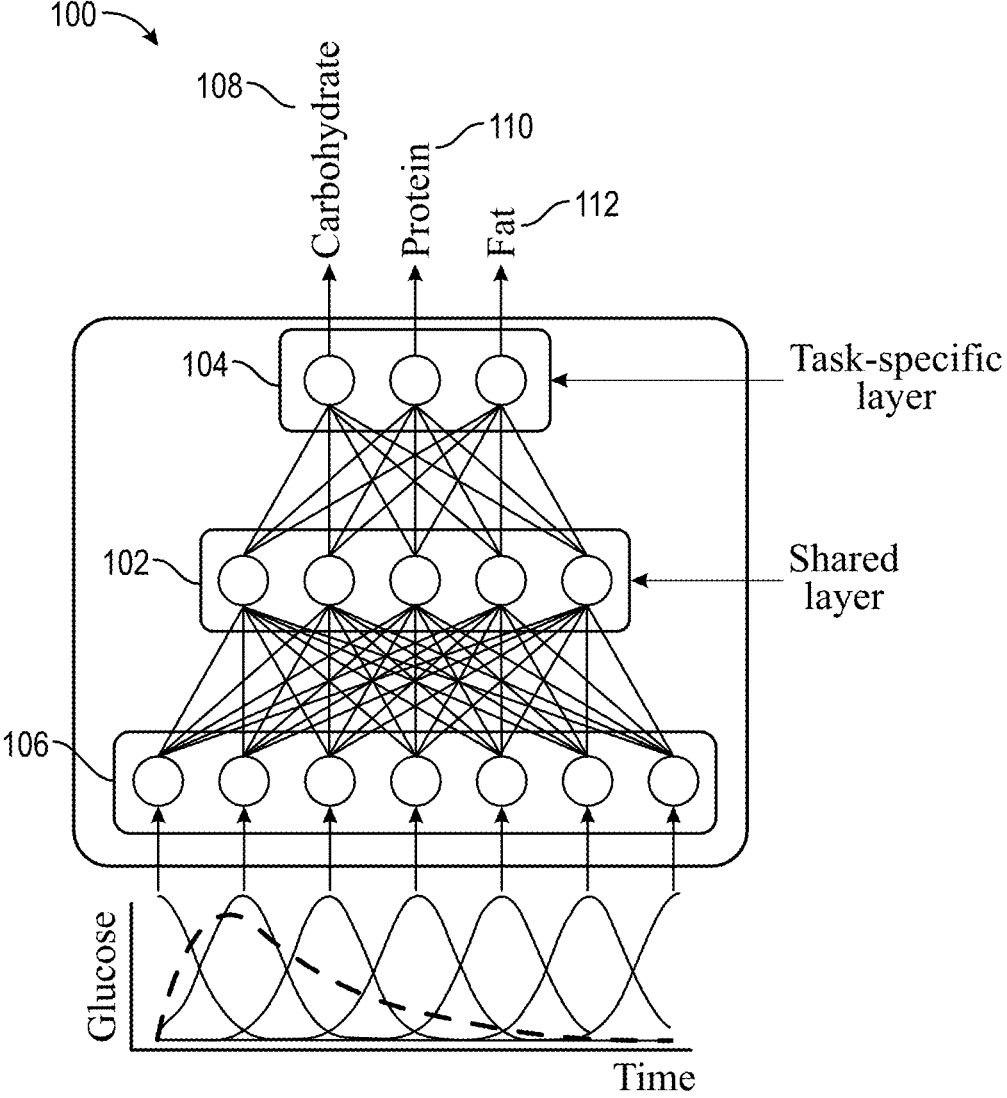
FIG. 2 is a schematic illustrating a multi-task neural network for estimating macronutrient composition from post-prandial glucose responses (i.e., glucose response after a meal) according to embodiments of the disclosure.

As the first embodiment, we developed a multi-task neural network having two layers: a fully-connected shared layer, designed to learn the shared impact among the three macronutrients, and a task-specific layer, designed to estimate each macronutrient. FIG. 2 illustrates a basic architecture for an illustrative multi-task neural network 100 that can be used to predict the macronutrient composition of meals from CGM data. Network 100 may be implemented by a computer comprising a processor and memory and includes a shared layer 102 that learns information common to the three macronutrients (i.e., carbohydrates, proteins, fats) and a task-specific layer 104 that predicts the amount of each individual macronutrient. Network 100 outputs as tasks 108, 110, 112 the predicted makeup of carbohydrates, proteins, and fats, respectively. The hidden units in the shared layer use a rectified linear unit (ReLU) activation function to capture non-linear information in the PPGR, and a linear activation function for the task-specific layer to span the full range of macronutrient levels. Input 106 is communicated to shared layer 102 from, for example, a CGM.

Figure 3:
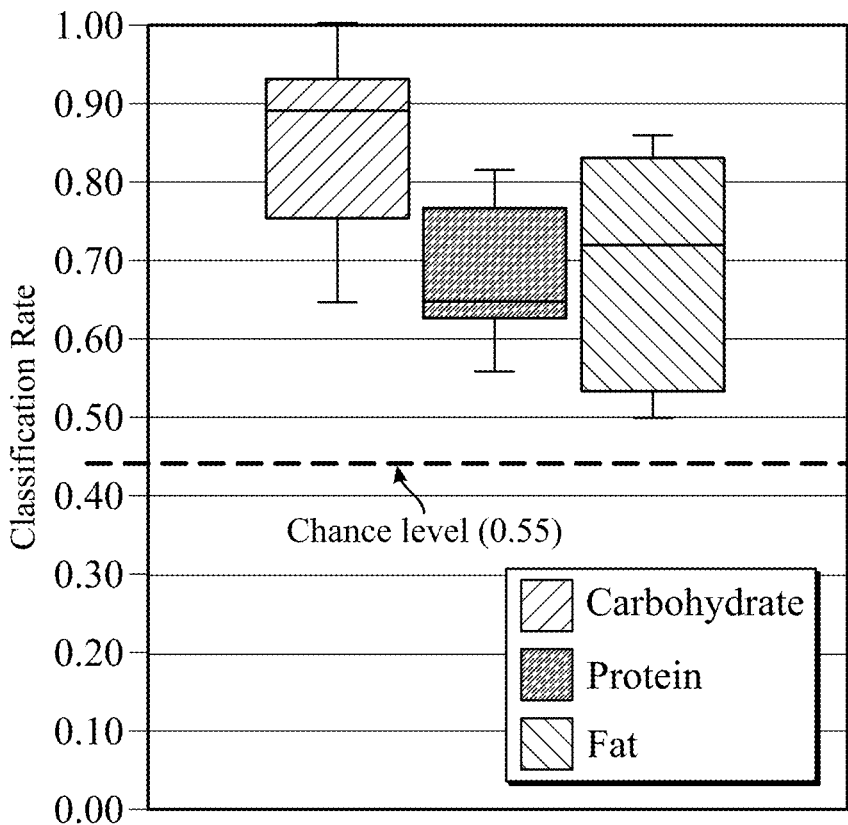
FIG. 3 is a graph showing ternary classification results (low, medium, high) for the three macronutrients (carbs, protein, fat) in the study.

We set up the neural network as a ternary classification model, where the goal was to predict the level (low: 1, medium: 2, high: 3; see Table 1) of the three macronutrients. We evaluated the network in a leave-one-subject-out fashion on 10 participants, i.e., we trained the network on 9 participants and tested it on the remaining participant, and we repeated the process 10 times. Results are shown in FIG. 3. The median classification rates for carbohydrates, proteins, and fats are 0.89, 0.65 and 0.72, all significantly above chance level (0.55), which clearly indicate that (1) the PPGR contains information that is related to the macronutrient composition of a meal, and (2) that the multi-task neural network is able to exploit this information to predict the meal's macronutrients.

2. Gradient Boosted Model

In another embodiment, a gradient boosted model was used in combination with a biomarker to predict the macronutrient composition of a consumed meal. As in the multi-task neural network, Gaussian AUCs were extracted from the PPGR (FIG. 1) and were then passed to the gradient boosted model, which had been trained as a regression model to estimate the amount of each macronutrient in a consumed meal (one model per macronutrient). The gradient boosted model is a decision-tree-based ensemble method that has achieved state-of-the-art performance across a variety of machine-learning competitions and industrial applications with small-to-medium sized datasets. The gradient boosted model builds a sequence of decision trees, each tree trained to reduce the prediction error on the previous trees, with errors being minimized using gradient descent. To optimize the model's hyperparameters, a grid-search was constructed via an internal cross-validation on training data, searching the depth of each decision tree (1 to 6), and number of estimators (20 to 200), keeping all the other parameters as default (0.1 learning rate). Model performance was evaluated in terms of two measures. The first measure is the Root Mean Squared Relative Error (RMSRE), calculated as:

$$RMSRE = \left(\frac{1}{N}\sum_{i=1}^{N}(y_i - \tilde{y}_i)^2 / y_i^2\right)^{\frac{1}{2}}$$ 
<div align="right">Equation 2</div> where $y_i$ and $\tilde{y}_i$ are the ground truth and predicted value of the amount of a macronutrient in the i-th meal. Using the RMSRE (instead of the more conventional RMSE) makes it easier to compare prediction performance for the three macronutrients since their ranges differ. The second measure, Pearson's correlation coefficient between the ground truth and predictions $\rho(y, \tilde{y})$, allows us to determine whether the predictions are consistent (i.e., increasing with increasing values of the dependent variables).

TABLE 2

Prediction results using gradient boosted model in terms of correlation coefficient between actual and predicted amounts of the macronutrients, and RMSRE (standard deviation in parentheses). All correlations are statistically significant at the $p < 0.0001$ level.

|  | Carbohydrates | Protein | Fat |
|---|---|---|---|
| Correlation coefficient | 0.872 | 0.471 | 0.650 |
| RMSRE | 0.241 (0.09) | 0.491 (0.1) | 0.434 (0.08) |

Prediction results for the gradient boosted model are summarized in Table 2. The actual and predicted amounts of the three macronutrients were highly correlated (p<0.0001), reaching correlation of 0.872 for carbohydrates, 0.471 for protein, and 0.650 for fat. Results in terms of the RMSRE were also positive: the gradient boost model was able to predict the actual amount of carbohydrates with an error of 24.1% (e.g., for a meal with 100 g of carbohydrates, the model would predict a carbohydrate level between 75 g and 125 g; for a meal with 10 g of carbohydrates, the model would predict that it is between 7.5 g and 12.5 g). The model was also able to predict the actual amounts of protein and fat, albeit with a higher error of 49.1% and 43.4%, respectively.

3. Multiple Biomarkers

In another embodiment of the invention, the use of additional biomarkers (e.g., amino acids and triglycerides) was examined to see if the prediction performance would be improved for the three macronutrients. During the pilot clinical study, concentrations of these additional biomarkers had been measured at various times following consumption of the standardized meals, resulting in response curves similar to the ones obtained for glucose using the CGMs (see FIG. 1 and FIG. 4). For each additional biomarker, five AUC features were extracted, as was done for the PPGR. Then, the gradient boosted model was retrained to take advantage of this additional biomarker information.

Results are summarized in Table 3 in terms of the correlation coefficient between actual and predicted amounts of macronutrients. The addition of amino acids had a large effect in the model's ability to predict protein, increasing the correlation coefficient from 0.42 to 0.72, which is to be expected since amino acids are the building blocks of protein. Likewise, adding triglycerides improves the model's ability to predict fat content, increasing the correlation coefficient from 0.49 to 0.58. Similar conclusions can be reached by analyzing the root mean squared relative error (RMSRE) of the prediction shown in Table 4. These results show that (1) additional information about the constituents of a meal can be obtained by measuring other biomarkers beyond glucose, and (2) that our computational models can exploit this additional information to improve the prediction performance.

TABLE 3

Prediction results using gradient boosted model in terms of correlation coefficient between actual and predicted amounts of the macronutrients. All correlations are statistically significant at the $p < 0.0001$ level.

|  | Carbohydrates | Protein | Fat |
|---|---|---|---|
| Glucose | 0.79 | 0.42 | 0.49 |
| Glucose + Amino Acids | 0.78 | 0.72 | 0.56 |
| Glucose + Triglycerides | 0.78 | 0.55 | 0.58 |
| Glucose + Amino Acids + Triglycerides | 0.78 | 0.75 | 0.62 |

TABLE 4

Prediction results using gradient boosted model in terms of RMSRE

|  | Carbohydrates | Protein | Fat |
|---|---|---|---|
| Glucose | 0.30 (0.12) | 0.54 (0.14) | 0.49 (0.15) |
| Glucose + Amino Acids | 0.28 (0.10) | 0.34 (0.14) | 0.46 (0.15) |
| Glucose + Triglycerides | 0.31 (0.09) | 0.46 (0.19) | 0.45 (0.18) |
| Glucose + Amino Acids + Triglycerides | 0.31 (0.09) | 0.30 (0.10) | 0.43 (0.19) |

A number of future directions for this work are possible. More subject-dependent factors could be incorporated in order to better understand the impact these factors have on the PPGR. Additionally, the quantity of known meals needed to rapidly train models can be explored. This includes exploring a wider feature space with respect to the CGM signals. Finally, physical activity has an impact on the PPGR. While this study limited the physical activity of the participants, removing that restriction will require incorporating activity recognition tasks with the diet monitoring work. While a number of related studies have focused on predicting the PPGR to different types of meals, this work predicted meal composition from CGM signals. This contribution enables automated logging of macronutrient composition for participants who wear a CGM, allowing for more accurate and timely monitoring of patient diet. With this more accurate data, the patient is able to make informed decisions about the composition of their meals to make desired changes to their glucose level.

The ability to track food intake automatically is a first step towards developing personalized behavioral interventions for obesity and other diseases that require dietary control (e.g., cardiovascular disease). Tracked eating patterns may be used to develop models of anticipation of high-risk relapse situations (e.g., times of day, social situations likely to lead to slip-ups in diet). Unexpectedly high readings of blood glucose may be used to engage patients in problem solving and help close gaps in understanding about the impact of certain foods. Combined with the ability to assess body responses (i.e., glucose excursions) of foods, the proposed algorithms can lead to new behavioral interventions that help participants make and understand better food choices.

By way of example, upon receiving analysis regarding a consumed meal, the individual (or the individual's nutritionist, doctor, etc.) may make changes to their future meal consumptions and/or an amount of a prescribed medication to improve or align their macronutrient intake and/or general health. For example, an individual may be on a diet plan with a goal of adhering to a specific macronutrient intake. In response to receiving analysis that a macronutrient level is high or low, the individual may make changes to their next meal to compensate for the high or low macronutrient level as appropriate (or a doctor may make changes to medications based upon a history of macronutrient intake). For example, if carbohydrate level is determined to be too high in a consumed meal (e.g., exceeds a value set out in a nutrition plan), the individual can consume fewer carbohydrates in the next meal to compensate. Using the methodologies disclosed herein, the individual has the ability to track their macronutrient intake with minimal effort compared to previous methodologies.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The term "at least one of" is meant to cover combinations of the listed elements, components, features, and the like, and the listed elements, components, features, and the like individually. For example, the phrase "at least one of A and B" is used to cover embodiments comprising only A, comprising only B, and comprising A and B unless stated otherwise.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A method, carried out by a computer comprising a processor and memory, of predicting a composition of a meal, the method comprising:

obtaining, via a wearable or implantable sensor of an individual, data relating to a concentration of at least one biomarker of the individual who consumed the meal;

analyzing the data to determine the composition of the meal, wherein the analyzing comprises:

extracting a plurality of features from the data, the plurality of features comprising an area under-the-curve, a time to peak value, a time to return to baseline, a slope value describing a response of the at least one biomarker after the meal is consumed, and a shape of a post-prandial response of the biomarker; and using a computational model that utilizes the plurality of features to predict an amount of carbohydrates, proteins, fats, and fiber in the meal; and sending the predicted amount of carbohydrates, proteins, fats, and fiber in the meal to a monitoring device.

2. The method of claim 1, wherein the at least one biomarker comprises one or more of a sugar, an amino acid, a lipid, an electrolyte, a mineral, a vitamin, and a metabolite.

3. The method of claim 1, wherein the feature is normalized relative to a baseline level of the at least one biomarker of the individual.

4. The method of claim 1, wherein the computational model comprises statistical learning techniques.

5. The method of claim 1, wherein the at least one biomarker is glucose and is measured with a continuous glucose monitor.

6. The method of claim 5, wherein a monitor in communication with the continuous glucose monitor logs the composition of the meal.

7. The method of claim 1, wherein the analyzing includes normalizing a response of the at least one biomarker relative to a body composition of the individual.

8. The method of claim 1, wherein the monitoring device is a part of a continuous glucose monitor.

9. The method of claim 1, wherein the monitoring device is a mobile application in communication with a continuous glucose monitor.

10. The method of claim 1, wherein the monitoring device is a mobile device in communication with a continuous glucose monitor.

* * * * *